United States Patent
Zamudio Ahumada et al.

(10) Patent No.: US 10,478,355 B2
(45) Date of Patent: Nov. 19, 2019

(54) ABSORBENT CORE

(71) Applicant: Grupo P.I. Mabe, S.A. de C.V., Puebla (MX)

(72) Inventors: Andrés Zamudio Ahumada, Puebla (MX); Mauricio Vázquez Arana, Puebla (MX); José Salcedo Agüallo, Puebla (MX)

(73) Assignee: GRUPE P.I. MABE, S.A. DE C.V., Puebla (MX)

( * ) Notice: Subject to any disclaimer, the term of this patent is extended or adjusted under 35 U.S.C. 154(b) by 1030 days.

(21) Appl. No.: 14/893,268

(22) PCT Filed: May 24, 2013

(86) PCT No.: PCT/IB2013/054317
§ 371 (c)(1),
(2) Date: Nov. 23, 2015

(87) PCT Pub. No.: WO2014/188236
PCT Pub. Date: Nov. 27, 2014

(65) Prior Publication Data
US 2016/0120711 A1   May 5, 2016

(51) Int. Cl.
*A61F 13/15*    (2006.01)
*A61F 13/532*   (2006.01)
(Continued)

(52) U.S. Cl.
CPC ...... *A61F 13/532* (2013.01); *A61F 13/15617* (2013.01); *A61F 13/15707* (2013.01);
(Continued)

(58) Field of Classification Search
CPC .......... A61F 13/15617; A61F 13/15707; A61F 13/531; A61F 13/532; A61F 2013/530343; A61F 2013/53051; A61F 2013/5307
See application file for complete search history.

(56) References Cited

U.S. PATENT DOCUMENTS

| 4,834,735 A | 5/1989 | Alemany et al. |
| 5,098,423 A | 3/1992 | Pieniak et al. |

(Continued)

FOREIGN PATENT DOCUMENTS

| ES | 2178930 A1 | 1/2003 |
| ES | 2213492 A1 | 8/2004 |

(Continued)

OTHER PUBLICATIONS

Translation of ES-2178930.*

(Continued)

*Primary Examiner* — Bradley H Philips
(74) *Attorney, Agent, or Firm* — Vivicar Law, PLLC

(57) ABSTRACT

The invention relates to an absorbent core intended for use in a disposable absorbent article, said core comprising an upper surface and a lower surface, a front portion and a rear portion, two longitudinal edges and two transverse edges, and being formed of three layers: an upper layer, an intermediate layer and a lower layer. The upper and lower layers contain less than 25% superabsorbent material. The intermediate layer has three zones with different specific weights: one receiving and distribution zone, one or more transition zones and one or more anti-leakage zones.

8 Claims, 1 Drawing Sheet

(51) Int. Cl.
*A61F 13/531* (2006.01)
*A61F 13/53* (2006.01)
(52) U.S. Cl.
CPC .... *A61F 13/531* (2013.01); *A61F 2013/5307* (2013.01); *A61F 2013/53051* (2013.01); *A61F 2013/530343* (2013.01)

(56) References Cited

U.S. PATENT DOCUMENTS

| | | |
|---|---|---|
| 5,149,335 A | 9/1992 | Kellenberger et al. |
| 5,275,592 A * | 1/1994 | Grizzaffi ............... A61F 5/4401 2/403 |
| 5,849,002 A | 12/1998 | Carlos et al. |
| 2003/0187413 A1 | 10/2003 | Fell |
| 2003/0234468 A1 | 12/2003 | Rangachari et al. |
| 2010/0137773 A1 | 6/2010 | Gross et al. |

FOREIGN PATENT DOCUMENTS

| | | |
|---|---|---|
| MX | 219792 | 4/2004 |
| MX | PA04000091 A | 6/2005 |
| MX | 249142 | 9/2007 |
| WO | 2006004464 A1 | 1/2006 |

OTHER PUBLICATIONS

Communication pursuant to Article 94(3) EPC in European App. No. 13 885 211.6, dated Oct. 20, 2017.
PCT International Search Report and Written Opinion for PCT/IB2013/054317, dated Oct. 11, 2013 (English Translation).

* cited by examiner

ABSORBENT CORE

TECHNICAL FIELD OF THE INVENTION

The present invention relates to an absorbent core. More particularly, the present invention relates to absorbent cores such as those used, but not limited to, in disposable diapers, incontinence diapers, training pants and sanitary towels. Still more particularly, the present invention relates to an absorbent core with zones of different specific weights and densities and formed into layers.

BACKGROUND OF THE INVENTION

The disposable absorbent articles such as disposable diapers, incontinence diapers, training pants and sanitary towels, are basically formed by an upper layer which allows for the passage of the liquid, a bottom impermeable layer and an absorbent core placed therebetween. The absorbent core is responsible for absorbing and retaining the liquid or semi-liquid exudates which permeate the upper layer of the article.

An absorbent core, besides complying with its primary objectives mentioned above, must be soft and flexible, so as to fit the user's body. In recent years, the market has tended to thin absorbent cores, in which, for achieving the suitable absorption and retention, superabsorbent materials have been used which may be mixed with the fibers of which the absorbent core is comprised by, or located on specific zones of the core. One of the most commonly used superabsorbent materials (SAP) in disposable absorbent articles are the sodium or potassium polyacrylate particles, yet other several synthetic or natural materials are known in the field which may be used as SAP in absorbent cores.

There are plenty of thin cores proposals that better conform to the baby's body and meet the needs of fluids absorption and retention. For example, U.S. Pat. No. 5,149,335 to Kellenberger, refers to a thin disposable diaper containing superabsorbent material within the core, ranging from 60 to 100% of SAP contained in a fibrous core. On the other hand, U.S. Pat. No. 5,098,423 to Heinz A. Pieniak, covers a thin diaper with such an arrangement that is very convenient for the user, since it is very narrow in the crotch portion and the user must not remain with his legs apart; the absorbent core of this diaper contains from 200 to 1500% of a superabsorbent hydrogel.

Mexican Patent No. 249,142 to Corona Carlos, covers an ultra thin absorbent core containing no absorbent material fibers, same only comprises a superabsorbent material located within a covering layer of a nonwoven material, which upper distributes the liquid before it permeates and is absorbed and retained by the superabsorbent material.

Furthermore, in order to streamline the operation of absorbent cores, there have been several developments incorporating zones with different specific weights and densities within an absorbent core, such is the case of the absorbent core described in U.S. Pat. No. 4,834,735 to Alemany, which covers an absorbent core with an acquisition zone and a storage zone which have different densities; the acquisition zone which is located in the front half of the core has a lower density than the rest of the core (storage zone), thus the liquid will be quickly collected by the acquisition zone and distributed and stored therein. However the liquid will very easily reach the side edges of the core as the high-density zone continues until the edges thereof; U.S. Pat. No. 5,849,002 to Corona Carlos, refers to an absorbent core comprised by 3 zones, fluid receiving zone, a primary storage zone and an anti-leakage zone, each zone has different densities and specific weights. Mexican patent MX 219,792, also to Corona Carlos, covers an absorbent core incorporating transition zones between the receiving and anti-leakage zones, in these transition zones, the density decreases gradually to avoid disruption of the core.

Nevertheless, there is still a need to develop thin absorbent cores that are soft and comfortable for the user as well as more efficient, which improve the absorption rate and liquid distribution characteristics, in this proposal, said efficiency is based in the combination of an absorbent core with layers and zones with different specific weights and densities. The core has a first upper absorbent material layer, preferably defibrated cellulose, a second absorbent material layer, preferably defibrated cellulose at the bottom of the core, and a third layer comprising a mixture of absorbent material fibers and superabsorbent material (SAP) particles, located between the first and second layers; moreover, the intermediate layer (third layer) has therein distribution-storage, transition and anti-leakage zones. Thus a thin, soft, flexible core is obtained with very good absorption rate and liquid distribution characteristics, further reducing the consumption of cellulose, and optimizing the use of the superabsorbent powder (SAP).

OBJECTS OF THE INVENTION

One object of the present invention is to provide a thin, soft, flexible absorbent core, with suitable absorption, distribution and retention characteristics.

Another object of the invention is to provide the proper SAP/CELLULOSE ratio in a thin core with different densities and specific weights zones and formed into layers.

A further object of the invention is that the superabsorbent material contained within the core does not migrate to the article surface.

Another object of the invention is to reduce the amount of cellulose fibers contained in the core improving the efficiency thereof.

A further object of the invention is to incorporate the core into a disposable absorbent article.

DETAILED DESCRIPTION OF THE INVENTION

The absorbent core of a disposable absorbent article is the portion thereof in charge of absorbing and containing liquids and semi-liquid exudates that reach it. The core must also have the ability to distribute and retain the liquid, preventing its return to the upper surface of the core and consequently to the upper of the article; on the other hand it should be smooth and conform to the user's body.

Hereinafter, the absorbent core of a disposable diaper is described, however this core may be incorporated into an absorbent insert, in a training pant, in a sanitary napkin, in a disposable diaper, or any other article aimed to absorb exudates and which is disposed after its use.

Figure 1:
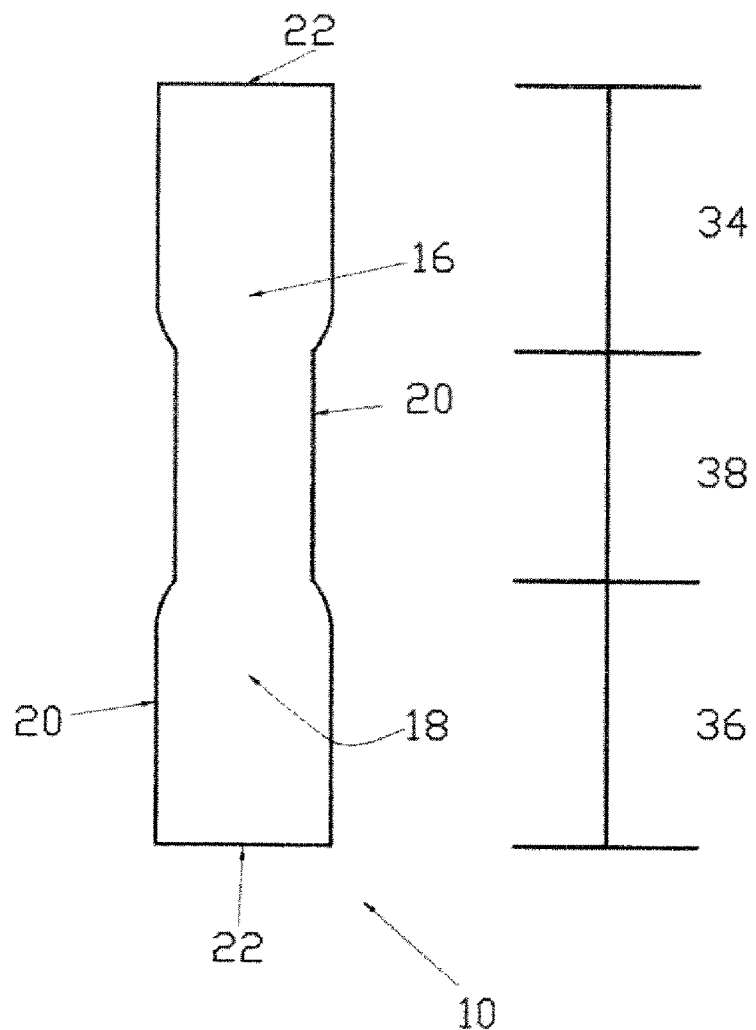
FIG. 1 shows the absorbent core of the present invention.

The absorbent core (10) of the present invention has a upper surface (16) and a lower surface (18); two longitudinal edges (20) and two transverse edges (22); the core (10) shown in FIG. 1 has an hourglass shape, with a front portion (34), a rear portion (36) and a central or crotch portion (38) which is narrower than the front and rear portions so that it is more comfortable for the user, however, the core of the invention can take any other form known in the art, as an example, the core (10) may be rectangular, "T"-shaped, "I" shaped, or any other straight or anatomical shape.

Figure 2:
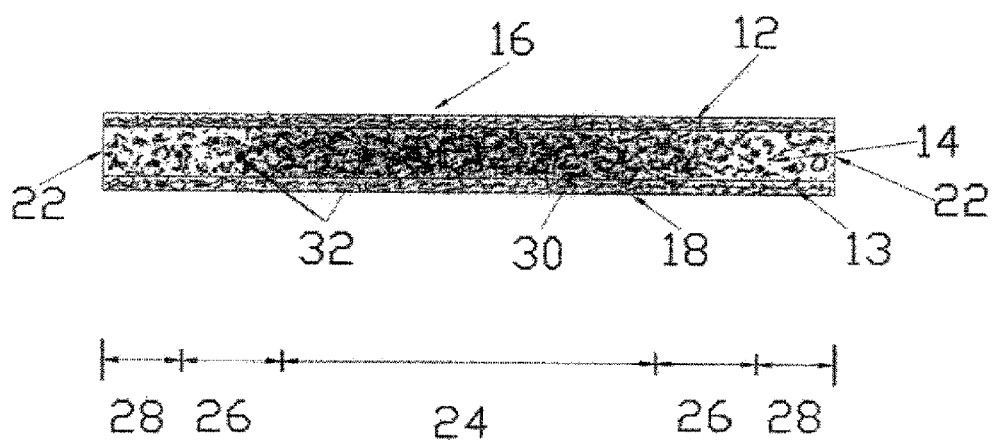
FIG. 2 is a side view of the absorbent core of the invention.

FIG. 2 shows a longitudinal section of the absorbent core (10) shown in FIG. 1, it may be seen that the core is formed of three layers: a upper layer (12) placed on the upper surface (16) of the core, a lower layer (13) placed on the lower surface (18) thereof and a intermediate layer (14) placed between the upper (12) and lower (13) layers.

The upper layer (12) is comprised, preferably by 100% of absorbent fibers, however, it may contain up to 25% of superabsorbent material (SAP) particles; its primary function is to provide softness and flexibility to the core, collects the liquid and quickly transfers it to the intermediate layer (14), besides it helps to contain the superabsorbent material contained in said intermediate layer (14), so that it will not reach the surface of the core avoiding the risk of contacting the user skin. Furthermore, since the upper layer (12) contains no or a low concentration of superabsorbent material particles, there is no blocking effect which could occur when said superabsorbent material swells when contacting the liquid, thus the upper layer (12) allows the free pass of the fluid into the intermediate layer faster than in cores containing high concentration of superabsorbent material at the upper portion (16).

The lower layer (13), as the upper layer (12) is comprised, preferably by 100% of fibers of absorbent material, although it may contain up to 25% of superabsorbent material mixed with fibers of absorbent material; it has two main functions: a) provide softness and flexibility to the core b) do not allow the superabsorbent material particles to reach the lower surface of the core. This is important since the absorbent core is to be incorporated into a disposable absorbent article and the bottom portion (18) of said core will be in contact with the outer layer of the article, if the particles of the superabsorbent material are in contact with the outer layer, they may weaken and even cause perforations to said outer layer.

The intermediate layer (14) of the absorbent core of the present invention, is comprised by a mixture of cellulose fibers (32) and superabsorbent material particles (30), it has the primary function of distribute and retain exudates as well as prevent the fluid from return to the upper portion of the core, and as a result, it prevents the return of fluids to the surface of the article to which it is incorporated. This intermediate layer (14) has, within same, well-defined zones with different specific weights and densities: a first distribution-storage zone (24), one or more transition zones (26) and one or more anti-leakage zones (28).

The distribution-storage zone (24) of the intermediate layer (14) has the highest concentration of absorbent material fibers and superabsorbent material particles such that upon receipt of the liquid, it efficiently distributes and stores it, avoiding its return. The distribution-storage zone (24) has a specific weight (g/m$^2$ of cellulose fibers+superabsorbent material) 35% to 50% greater than the average specific weight of the transition zones (26) and 75% to 100% greater than the specific weight of the anti-leakage zones (28).

On the other hand, the receiving-storage zone (24) has a density A, the anti-leakage zones (28) have a density B, and the transition zone(s) (26) has(ve) a density which varies along the same between A and B. The density A is greater than the density B. Because of this difference in density and applying the capillarity theory, the spaces between fibers in the distribution-storage zone (24) are smaller, causing a greater fluid distribution. Furthermore, the cellulose fibers are homogeneously mixed with SAP particles, so that when contacting the fluid, the latter absorb and retain it, while the fibers which are adjacent thereto help the fluid which is not absorbed to continue its distribution and may, in turn, be absorbed and retained.

In the transition zones (26), the density is gradually reduced from A to B, so, the distribution rate of the fluid is also reduced and the fluid is stored in the spaces between fibers and within the SAP particles. Finally, in the anti-leakage zones, the density B is even lower, such that the fluid is accommodated between the fibers and does not reach the transverse edges (22) of the core.

Fibers of cellulose are used generally as the absorbent material of the core, although other known absorbent materials may be used such as cotton, rayon, etc. As superabsorbent material particles the preferably used ones are sodium or potassium polyacrylate particles, but any other natural or synthetic superabsorbent materials may be used.

The layered absorbent core in of the present invention, provides optimum functionality, quickly collects the fluid, distributes and retains it such that most of the core is used, and the fluid does not reach the transverse edges of the core. Furthermore, the core is soft and flexible, since the upper (12) and lower layers (13) thereof are comprised mainly of absorbent material fibers (30). The low concentration of SAP in the upper and lower surfaces of the core prevents: a) that this material could contact with the user skin; b) that there may be breaking or weakening of the lower layer of the disposable absorbent article to which the core (10) is incorporated and c) blocking the upper portion of the core due to the swelling of the superabsorbent particles.

The core (10) of the invention may be incorporated into any type of disposable absorbent article, such as disposable diapers, training pants, sanitary napkins or absorbent inserts (an absorbent insert is an article comprised by a upper layer, a lower layer and an absorbent core (10) located therebetween).

A further advantage of the core (10) of the invention is that it is possible to decrease the amount of absorbent material used without affecting the functionality of the core, resulting in substantial savings, as can be seen in the following examples:

Example 1

Traditional Core: Bio Baby Diaper size 4 manufactured in December 2010.
Core (10): Bio Baby Diaper size 4 with new core

|  | Traditional Core | Core (10) |
|---|---|---|
| Cellulose weight (g) | 19 | 16.5 |
| SAP weight (g) | 12.5 | 12 |

| Functional Characteristics Diaper | | |
|---|---|---|
| Third permeation time (sec) | 125 | 115 |
| 3rd rewet (g) | 0.96 | 0.31 |
| Longitudinal distribution distance (cm) | 31 | 36 |

Example 2

Traditional core: Moltex Diaper size 4 manufactured in December 2010.
Core (10): Moltex Diaper size 4 with new core

|  | Traditional Core | Core (10) |
|---|---|---|
| Cellulose weight (g) | 17 | 14 |
| SAP weight (g) | 11.5 | 10.5 |

| Functional characteristics of the diaper | | |
|---|---|---|
| Third permeation time (sec) | 120 | 117 |
| 3rd rewet (g) | 0.66 | 0.11 |
| Longitudinal distribution distance (cm) | 29 | 35 |

Test Methods
Return of fluids to the surface of a diaper (rewet), permeation time and fluid distribution.
Material and equipment to be used
1.1.1 Inspection table.
1.1.2 Electronic scale
1.1.3 Chronometer
1.1.4 Separating funnel adjusted to 7+/−1 ml/s or the like
1.1.5 Beaker
1.1.6 150 ml graduated cylinder
1.1.7 Weigh with 3.5 kg acrylic receiving cylinder, 10 cm. OD and 2.54 cm. ID and 22 cm height (for adult and baby diaper) (0.7 PSI)
1.1.8 2.5 kg weigh with 8 cm. diameter base. (0.7 psi)
1.1.9 Adhesive tapes
1.1.10 Synthetic urine (solution of purified or distilled water and 0.9% NaCl)
1.1.11 Tissue paper boxes and undefibered cellulose 10×10 cm
1.2 Development
1.2.1 Weigh the sample and record data.
1.2.2 Place the product extended on the working table with the inner cover (Non Woven) upwards, the diaper tapes to the opposite of the person performing the test and secure it by the corners with adhesive tape.
1.2.3 Make a mark on the center of the product from the front edge of the core, at a distance according to Table No. 1

TABLE NO. 1

| Size | Centimeters |
|---|---|
| RN, 1 | 11 |
| 2 | 12 |
| 3 | 13 |
| 4 | 15 |
| 5 and 6 | 17 | inside the cylinder.
1.2.6 Pour or meter the appropriate amount of synthetic urine according to the product.
1.2.7 Measure the time from the opening of the key of the separating funnel until the synthetic urine is completely absorbed; record the data as the first permeation time.
1.2.8 Let stand for 10 minutes and remove the weigh with the dispenser mentioned in step 5.1.7.
1.2.9 Immediately after, weight a 10×10 cm cellulose box, record as P1, place it on the discharge so that it is in contact with the sample and centered with respect to the point of urination, place the weigh mentioned in step 5.1.8 on the box, for 2 minutes.
1.2.10 During those two minutes measure the length achieved by the synthetic urine and register it as first longitudinal distribution distance.
1.2.11 After the 2 minutes, remove the weigh.
1.2.12 Immediately thereafter pass the cellulose, recording the data as P2.
1.2.13 For the second and third REWET, repeat steps 5.2.6 to 5.2.14, the second and third permeation times and the second and third longitudinal distribution distance are also recorded.
1.3 Calculations.
1.3.1 REWET=P1-P2

In one of the embodiments, both the lower layer (13) and the upper layer (12) comprise from 75% to 100% absorbent material fibers, they also comprise from 0 to 25% of superabsorbent materials; likewise, a combination of a upper layer comprising from 75% to 100% absorbent material fibers and from 0% to 25% of superabsorbent material may also be realized, while the lower layer only comprises 100% of absorbent material fibers and vice versa.

The present invention further refers to a method of forming the core (10) which comprises the following steps:
forming the lower layer (13) and the upper layer (12) comprising from 75% to 100% of fibers of absorbent material and 0% to 25% of superabsorbent particles;
forming the intermediate layer (14) with a distribution-storage zone (24) with a specific weight (g/m² of cellulose fibers+superabsorbent material) 35% to 50% greater than the average specific weight of the transition zones (26) and from 75% to 100% greater than the specific weight of the anti-leakage zones (28);
Perform the appropriate cuts, according to the shape of the desired absorbent core
Place the absorbent core made with the knowledge of the present description in, but not limited to, disposable diapers, incontinence diapers, training pants and sanitary napkins.

While the invention has been described in terms of a presently preferred embodiment, various obvious changes and modifications thereof may be made, such changes and modifications are within the spirit and scope of the invention as defined in the appended claims.

The invention claimed is:

1. An absorbent core for use in a disposable absorbent article having a upper surface and a lower surface, a front portion, a rear portion and a crotch portion, two longitudinal edges and two transverse edges, wherein the absorbent core is formed of three layers: an upper layer, an intermediate layer and a lower layer, such that:
the upper and lower layers are comprised by a homogeneous mixture of fibers of absorbent material and particles of superabsorbent material and the particles of superabsorbent material are present in the upper and lower layers in a concentration lower than 25% by weight, wherein the upper and lower layers are not comprised 100% by fibers of absorbent material,
the intermediate layer is comprised by fibers of absorbent material homogeneously mixed with particles of superabsorbent material and has three zones with different specific weights: an acquisition-distribution zone; one or more transition zones; and one or more anti-leakage zones, in which the specific weight in g/m2 of absorbent material plus superabsorbent material of the acquisition-distribution zone of the intermediate layer is 75% to 100% greater than the specific weight in g/m2 of absorbent material plus superabsorbent material of the one or more anti-leakage zones, the specific weight in g/m2 of absorbent material plus superabsorbent material of the acquisition-distribution zone of the intermediate layer is 30 to 50% greater than an average specific weight of absorbent material plus superabsorbent material of the one or more transition zones, and the specific weight expressed in g/m2 of superabsorbent material plus absorbent material of the one or more transition zones of the intermediate layer gradually decreases towards the transverse edges of the core.

2. The absorbent core for use in a disposable absorbent article as described in claim 1, wherein the fibers of absorbent material are cellulose fibers.

3. The absorbent core for use in a disposable absorbent article as described in claim 1, wherein the superabsorbent material is sodium or potassium polyacrylate particles.

4. A disposable diaper comprising the absorbent core according to claim 1.

5. A training pant comprising the absorbent core according to claim 1.

6. A sanitary towel comprising the absorbent core according to claim 1.

7. An absorbent insert comprising the absorbent core according to claim 1.

8. An absorbent care for use in a disposable absorbent article as described in claim 1, wherein the acquisition-distribution zone has a density A, the one or more anti-leakage zones have a density B, and the one or more transition zones have a density which varies along the same between A and B, being the density A greater than the density B, and the density is gradually reduced from A to B in the one or more transition zones.

* * * * *